United States Patent [19]

Morrison

[11] Patent Number: 5,171,977
[45] Date of Patent: Dec. 15, 1992

[54] PORTABLE MEDICAL SPECIMEN DATA COLLECTION SYSTEM

[75] Inventor: Robert L. Morrison, Tucson, Ariz.

[73] Assignee: Sunquest Information Systems, Inc., Tucson, Ariz.

[21] Appl. No.: 523,109

[22] Filed: May 14, 1990

[51] Int. Cl.⁵ ............................................. G06F 15/42
[52] U.S. Cl. .................................. 235/375; 364/413.02
[58] Field of Search ....................... 235/375, 462, 472; 364/413.01, 413.02, 413.03

[56] References Cited

U.S. PATENT DOCUMENTS

| | | | |
|---|---|---|---|
| 3,831,006 | 8/1974 | Chaffin et al. | 235/375 |
| 3,848,112 | 11/1974 | Weichselbaum et al. | |
| 4,164,320 | 8/1979 | Irazoqui et al. | 235/375 |
| 4,476,381 | 10/1984 | Rubin | |
| 4,614,366 | 9/1986 | North et al. | |
| 4,628,193 | 12/1986 | Blum | 235/375 |
| 4,678,894 | 7/1987 | Shafer | 235/375 |
| 4,730,849 | 3/1988 | Siegel | |
| 4,853,521 | 8/1989 | Claeys et al. | 235/375 |
| 4,857,713 | 8/1989 | Brown | 235/375 |
| 4,857,716 | 8/1989 | Gombrich et al. | 235/375 X |

*Primary Examiner*—Robert Weinhardt
*Attorney, Agent, or Firm*—Kirkpatrick & Lockhart

[57] ABSTRACT

A system for collecting data relating to medical specimens includes a hand-held terminal incorporating a bar code reader and a keyboard for receiving information for identifying a medical specimen and a medical specimen source, an internal memory within the hand-held terminal for storing information including information identifying medical specimens and corresponding medical specimen sources, and application software operating within the hand-held terminal responsive to the input devices and the internal memory for verifying that the medical specimen identified by the received information should properly be collected from the medical specimen source identified by the received information. An LCD display, LEDs and an audible signal indicate whether the medical specimen identified by the received information should properly be collected from the medical specimen source identified by the received information. The hand-held terminal also functions to store in its internal memory information identifying a time at which the medical specimen is collected from the medical specimen source and information identifying alphanumeric codes relating to procedures performed in collecting the medical specimen from the medical specimen source.

15 Claims, 10 Drawing Sheets

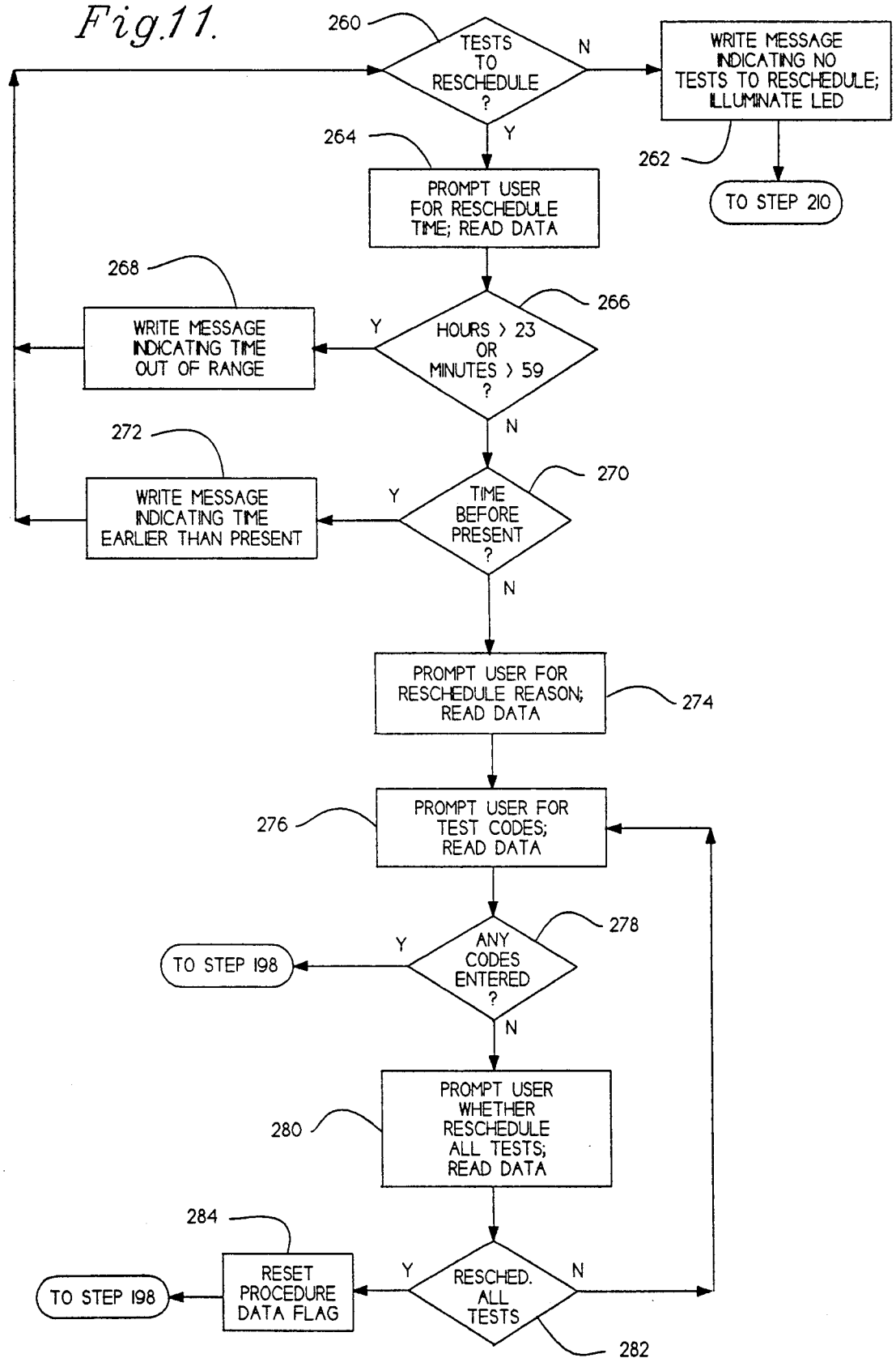

PORTABLE MEDICAL SPECIMEN DATA COLLECTION SYSTEM

BACKGROUND OF THE INVENTION

1. Field of the Invention

The present invention is directed generally to a system and method for performing automated data collection with a portable device and more specifically to a system and method for performing automated data collection relating to medical specimens with a portable device.

2. Description of the Prior Art

In the practice of medicine, it is often necessary to take specimens of a patient's body fluids or tissues for analysis in a laboratory to aid in the diagnosis and treatment of disease. In the present method of obtaining fluid or tissue samples from a patient, the phlebotomist is provided with a paper list of patients and the type of samples that are to be taken from each patient. Many laboratories produce these lists from a computer based automated information management system that controls the flow of data within the laboratory. However, all of the advantages of such a system are not available to the phlebotomist who does not have access to the system as he moves throughout the hospital collecting the required samples. Were such access available, it would be possible to automatically identify the correct patient and be certain of obtaining all of the desired specimens. In addition, any notes or changes to test orders could be directly entered without the need for manual transcription and later entry into the laboratory information system. Thus, the need exists for a portable hand-held device that will interface with the laboratory information system and will provide the phlebotomist both with the laboratory information system data which is pertinent to the collection of samples from patients and the ability to enter data directly into the portable hand-held device for later processing by the laboratory information system.

SUMMARY OF THE INVENTION

The present invention is directed to a portable data collection system for collecting data relating to medical specimens. The system includes input means for receiving information for identifying a medical specimen and a medical specimen source, memory means for storing information including information identifying medical specimens and corresponding medical specimen sources, means responsive to the input means and the memory means for verifying that the medical specimen identified by the received information should properly be collected from the medical specimen source identified by the received information, and output means responsive to the means for verifying for indicating whether the medical specimen identified by the received information should properly be collected from the medical specimen source identified by the received information. The system further includes first means responsive to the input means for storing in the memory means information identifying a time at which the medical specimen is collected from the medical specimen source, and second means responsive to the input means for storing in the memory means information identifying alphanumeric codes relating to procedures performed in collecting the medical specimen from the medical specimen source.

The present invention is also directed to a method for collecting data relating to medical specimens. The method includes the steps of receiving information for identifying a medical specimen and a medical specimen source, storing information including information identifying medical specimens and corresponding medical specimen sources, verifying that the medical specimen identified by the received information should properly be collected from the medical specimen source identified by the received information, and indicating whether the medical specimen identified by the received information should properly be collected from the medical specimen source identified by the received information. The method further includes the steps of storing information identifying a time at which the medical specimen is collected from the medical specimen source, and storing information identifying alphanumeric codes relating to procedures performed in collecting the medical specimen from the medical specimen source.

The present invention fulfills the need which exists for a portable hand-held device that will interface with the laboratory information system and will provide the phlebotomist both with the laboratory information system data which is pertinent to the collection of samples from patients and the ability to enter data directly into the portable hand-held device for later processing by the laboratory information system. These and other advantages and benefits of the present invention will become apparent from the description of a preferred embodiment hereinbelow.

BRIEF DESCRIPTION OF THE DRAWINGS

In order that the present invention may be clearly understood and readily practiced, preferred embodiments will now be described, by way of example only, with reference to the accompanying figures wherein:

FIGS. 3-11 depict flow charts illustrating the steps performed by the hand-held terminal of the system of FIG. 1;

DETAILED DESCRIPTION OF THE PREFERRED EMBODIMENT

Figure 1:
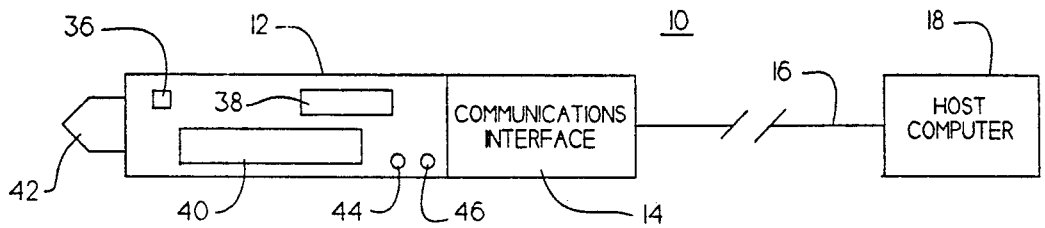
FIG. 1 illustrates a portable data collection system constructed according to the teachings of the present invention.

FIG. 1 illustrates a portable data collection system 10 of the present invention. Like reference numerals are employed among the various figures to designate like elements. The portable data collection system 10 includes a portable battery-operated hand-held terminal 12, a communications interface 14, a communications link 16 and a host computer 18. Hand-held terminal 12 includes an "on/off" key 36, an LCD screen 38, a keyboard 40, a bar code reader 42, a green-colored LED 44 and a red-colored LED 46.

Figure 2:
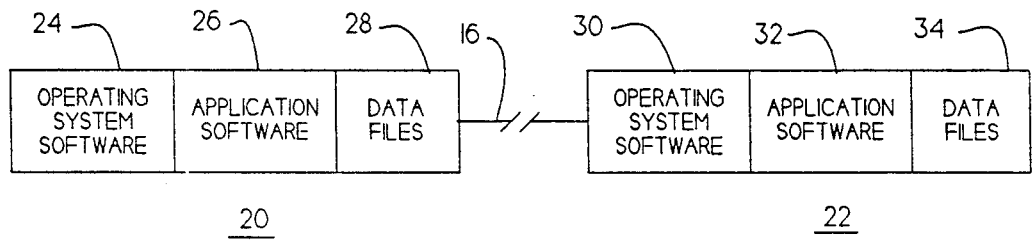
FIG. 2 illustrates, in block diagram form, the internal memory of the hand-held terminal of the system of FIG. 1 and the internal memory of the host computer of the system of FIG. 1.

FIG. 2 illustrates, in block-diagram form, the contents of the internal memory 20 of the hand-held terminal 12 as well as the internal memory 22 of the host computer 18. Operating system software 24, application software 26 and sequential data files 28 are contained within the internal memory 20 of the hand-held terminal 12. Similarly, operating system software 30, application software 32 and sequential data files 34 are contained within the internal memory 22 of the host computer 18. The details of operating system software 24 and operating system software 30 are not disclosed herein, however, each may be of a type generally known to those of ordinary skill in the art. As this invention is directed to the hand-held terminal 12 and application software 26 contained within the internal memory 20 of the hand-held terminal 12, the details of the application software 32 contained within the internal memory 22 of the host computer 18 are disclosed only to the extent necessary to properly explain the operation of the hand-held terminal 12 and the application software 26.

The operation of the hand-held terminal 12 and application software 26 will be explained through the use of flow charts illustrated in FIGS. 3-11. When the "on/off" key 36 of hand-held terminal 12 shown in FIG. 1 is depressed, the operating system software 24 causes the application software 26 to be activated. The entry point for the application software 26 is illustrated in the flow chart of FIG. 3 at step 100 which is labeled "Begin". Program control continues with step 102 where the user is prompted by a message displayed on LCD screen 38 of hand-held terminal 12 to select one of the following functions: "Load", "Dump", "Start" or "Quit". The application software 26 determines, at step 104, whether the "Load" function has been selected. If the "Load" function has been selected, program control is transferred to step 120 shown in FIG. 4. If the "Load" function has not been selected, program control continues with step 106 where the application software 26 determines whether the "Dump" function has been selected. If the "Dump" function has been selected, program control is transferred to step 140 shown in FIG. 5. If the "Dump" function has not been selected, program control continues with step 108 where the application software 26 determines whether the "Start" function has been selected. If the "Start" function has been selected, program control is transferred to step 160 shown in FIG. 6. If the "Start" function has not been selected, program control continues with step 110 where the application software 26 determines whether the "Quit" function has been selected. If the "Quit" function has been selected, an exit is made from application software 26; control of the hand-held terminal 12 is then returned to the operating system software 24 and the hand-held terminal 12 is turned off. If the "Quit" function has not been selected, program control is returned to step 102 where the user is again prompted to select one of the four available functions.

Figure 4:
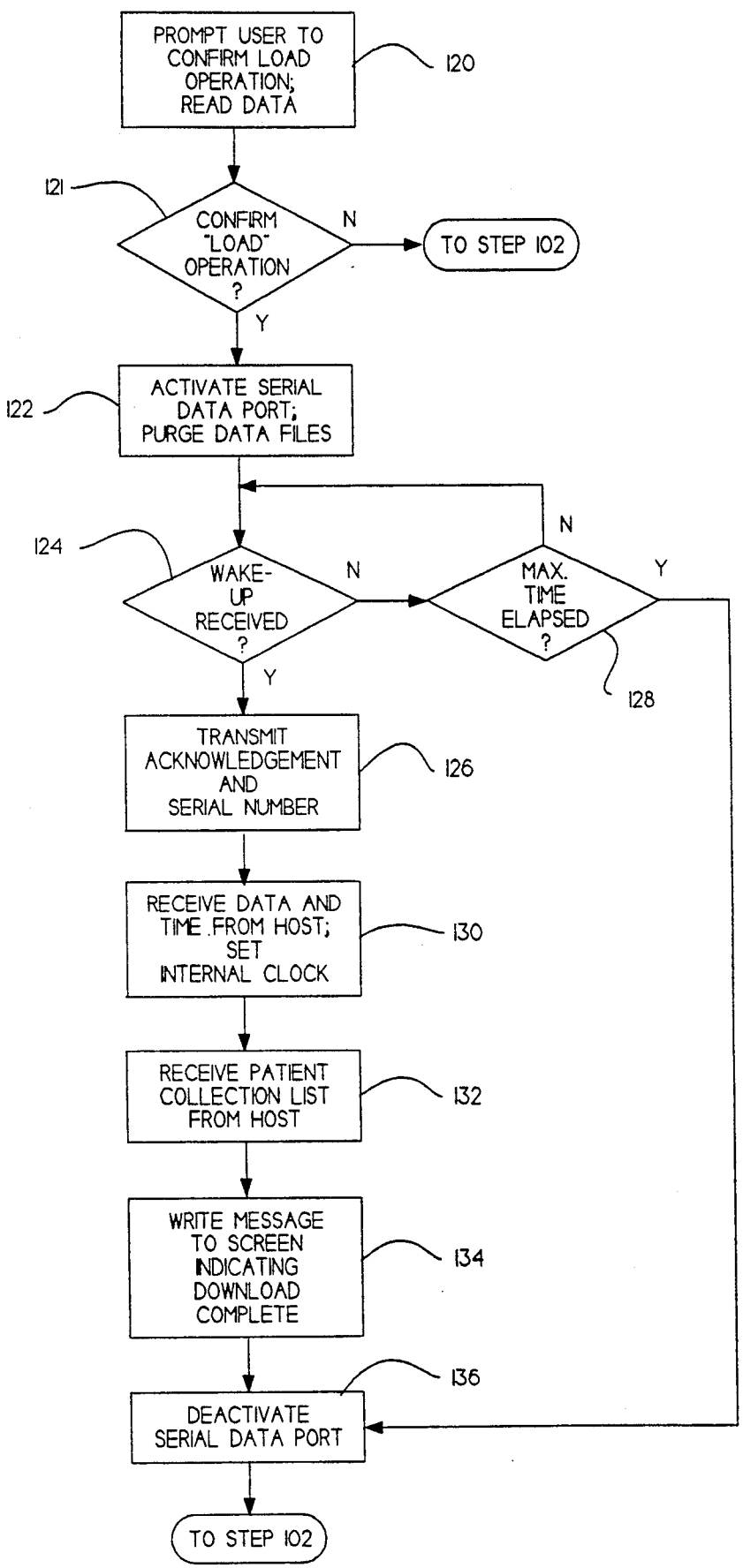

If the application software 26 has determined, in step 104, that the "Load" function has been selected, program control is transferred to step 120 illustrated in FIG. 4 where the user is prompted via LCD screen 38 to confirm that a "Load" operation is desired. If the application software 26 determines, in step 121, that the user has indicated that a "Load" operation is not desired, program control is returned to step 102 where the user is again prompted to select one of the functions "Load", "Dump", "Start" or "Quit". If the application software 26 determines, in step 121, that the user has confirmed that a "Load" operation is desired, program control continues with step 122 where a serial data port (not shown) in the communications interface 14 is activated and all sequential data files 28 in the hand-held terminal 12 are purged so that new data may be received. The application software 26, in step 124, then determines whether a "wake-up" character has been received from the host computer 18. The "wake-up" character is of a type generally known to those skilled in the art. If the "wake-up" character has been received from the host computer 18, program control continues with step 126. If the "wake-up" character has not been received from the host computer 18, the application software 26 determines, in step 128, whether a maximum time in which to receive the "wake-up" character has expired. This maximum time is user definable and relates to the design of the communications interface 14, the application software 26 and the application software 32 of host computer 18. If the maximum time in which to receive the "wake-up" character has expired, the application software 26 assumes that a communications error has occurred and program control is transferred to step 136 where the serial data port (not shown) of the hand-held terminal 12 is deactivated. If the maximum time in which to receive the "wake-up" character has not expired, program control is returned to step 124 to again determine whether the "wake-up" character has been received.

If the application software 26 determines, in step 124, that the "wake-up" character has been received from the host computer 18, then the hand-held terminal 12, in step 126, transmits an acknowledgment of the receipt of the "wake-up" character to the host computer 18 along with the serial number of the hand-held terminal 12. In step 130, the hand-held terminal 12 receives the current date and time from the host computer 18; an internal clock (not shown) of the hand-held terminal 12 is then set with the current date and time.

Figure 12:
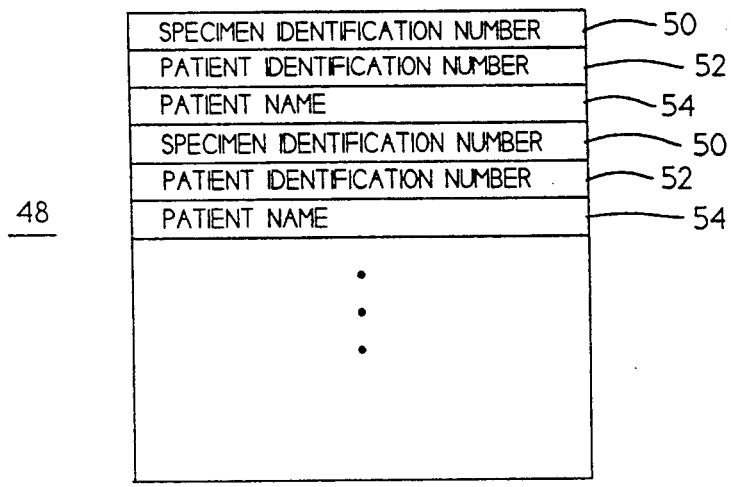
FIG. 12 illustrates a patient collection list stored within the internal memory of the hand-held terminal of FIG. 1.
Figure 14:
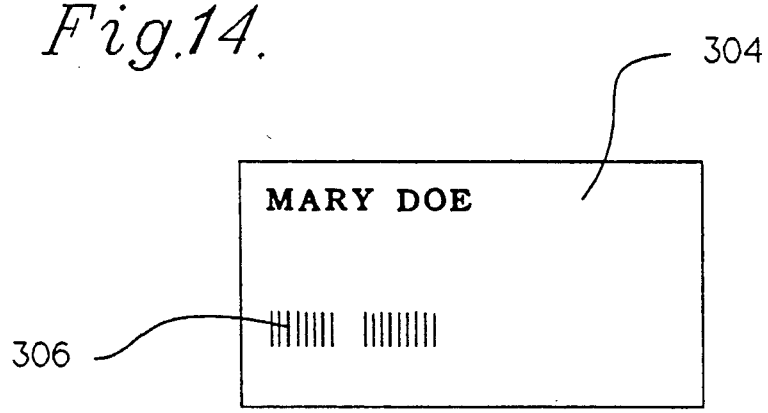
FIG. 14 illustrates a medical specimen label with which the present is used.

Program control continues with step 132 where a patient collection list 48 illustrated in FIG. 12 and contained within the sequential data files 34 of host computer 18 is received by the hand-held terminal 12 via communications interface 14 and communications link 16. The patient collection list is a sequential file; each entry of the patient collection list contains a specimen identification number 50, a patient identification number 52 and a patient name 54. After the entire patient collection list 48 has been received from the host computer 18, a message is displayed on the LCD screen 38, in step 134, notifying the user that the data download has been completed. The phlebotomist also receives, from the laboratory information system, printed specimen labels 304 (FIG. 14) for identifying the collected specimens. These specimen labels 304 contain the patient's name, hospital location, specimen type, specimen, tests, specimen identification number and a bar code 306 (FIG. 14) representation of the specimen identification number. The serial data port (not shown) of the hand-held terminal 12 is then deactivated in step 136. The hand-held terminal is now ready for use by the phlebotomist. Program control is returned to step 102 where the user is again prompted to select one of the four available functions.

Figure 5:
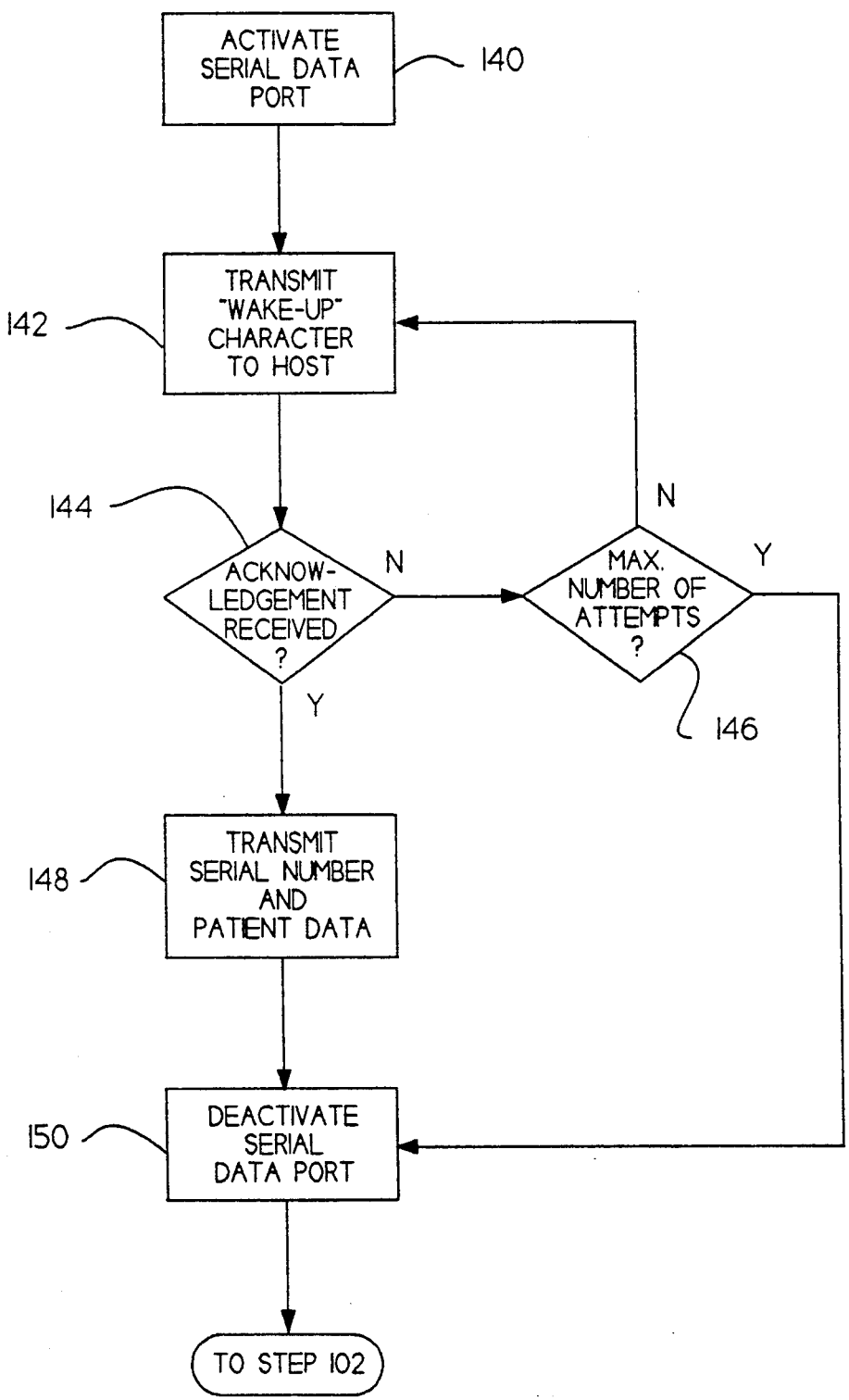

If the application software 26 determines, in step 106, that the "Dump" function was selected by the user, program control is transferred to step 140, illustrated in FIG. 5, where the serial data port (not shown) of the communications interface 14 is activated. The application software 26 then transmits a "wake-up" character to the host computer 18 in step 142. In step 144, the application software 26 determines whether an acknowledgment to the "wake-up" character has been received by the hand-held terminal 12 from the host computer 18. If an acknowledgment has not been received, the application software 26 determines, in step 146, whether the maximum number of attempts at sending a "wake-up" character to the host-computer has been made. This maximum number of attempts is user definable and relates to the design of the communications interface 14, the application software 26 and the application software 32 of host computer 18. If the maximum number of attempts has not been made, program control is returned to step 142 where another "wake-up" character is transmitted to the host computer 18. If the maximum number of attempts has been made, the application software 26 assumes that a communications error has occurred and program control is transferred to step 150 where the serial data port (not shown) of the communications interface 14 is deactivated. If the application software 26 has determined, in step 144, that an acknowledgment has been received, the serial number of the hand-held terminal 12 along with the contents of the sequential data files 28 are transmitted to the sequential data files 34 of host computer 18 via communications interface 14 and communications link 16. The serial data port (not shown) is then deactivated in step 150. The sequential data files 34 of host computer 18 are now ready for processing by application software 32. Program control is then returned to step 102 where the user is again prompted to select one of the four available functions.

Figure 6:
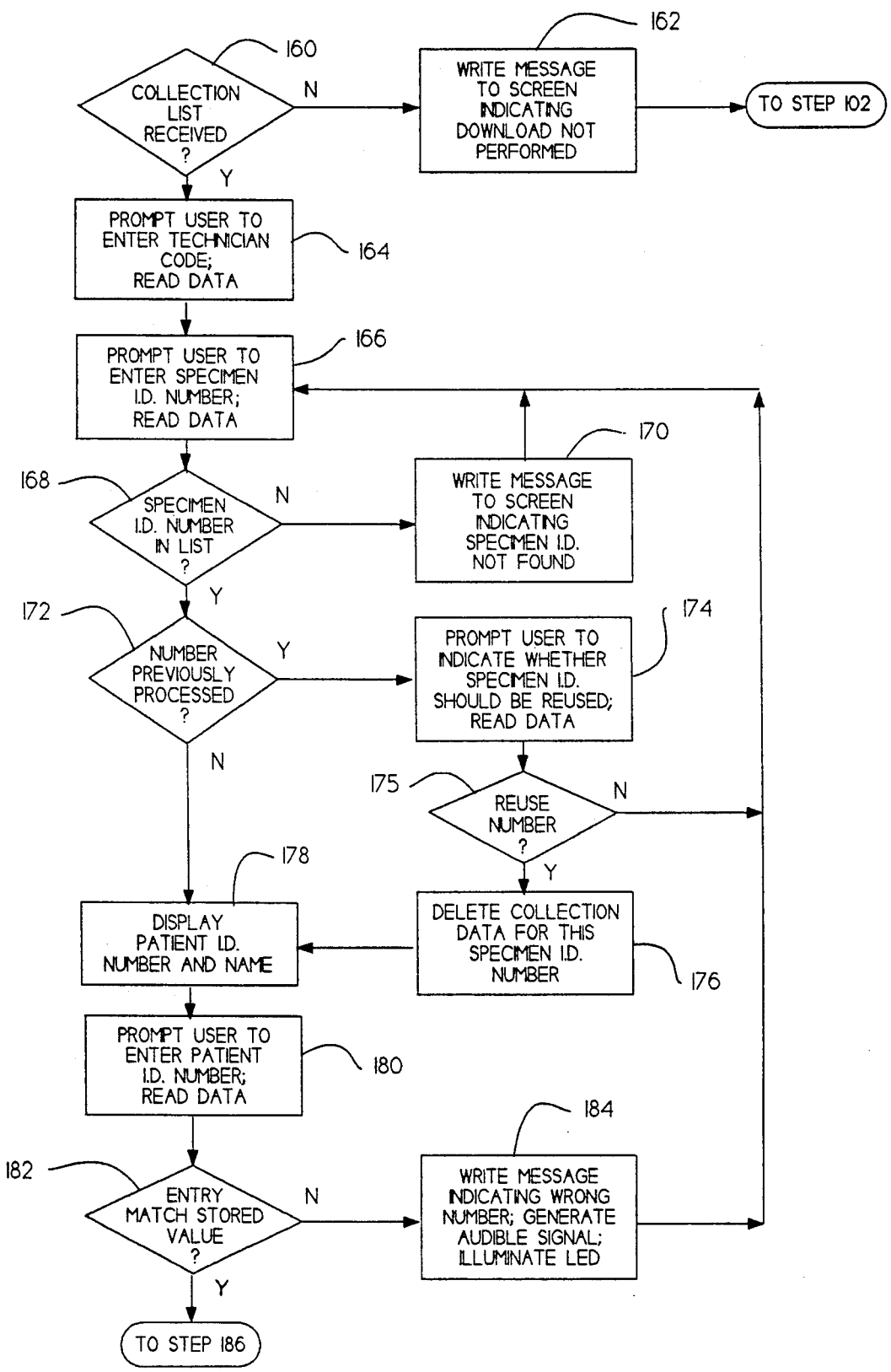

If the application software 26 determines, in step 108, that the "Start" function was selected by the user, program control is transferred to step 160 illustrated in FIG. 6 where the application software 26 determines whether the patient collection list 48 has been downloaded from the host computer 18. If the patient collection list 48 has not been downloaded, program control continues with step 162 where a message is written to LCD screen 38 indicating that the data download has not been performed. Program control is then returned to step 102 where the user is again prompted to select one of the available functions. If the application software 26 determines, in step 160, that the patient collection list has been downloaded, program control continues with step 164 where the user is prompted to enter his technician code. Entry of this code as well as all other data may be performed through either the keyboard 40 of hand-held terminal 12 or bar code reader 42 of hand-held terminal 12. The technician code is stored in the sequential data files 28. Program control then continues with step 166 where the user is prompted to enter a specimen identification number which is found on the specimen labels 304 (FIG. 14) provided by the laboratory information system.

In step 168, the specimen identification number which has been entered by the user is compared to the specimen identification numbers 50 in the patient collection list 48. If the user entered specimen identification number cannot be found in the patient collection list 48, program control is transferred to step 170 where a message is written to the LCD screen 38 indicating that the specimen identification number cannot be found in the patient collection list 48. Program control is then returned to step 166 where the user is again prompted to enter a specimen identification number.

If the user entered specimen identification number was found in the patient collection list 48, program control continues with step 172 where the application software 26 determines whether the user entered specimen identification number was previously processed. If the application software 26 determines that the user entered specimen identification number was previously processed, program control continues with step 174 where the user is prompted via LCD screen 38 to indicate whether he wishes to reuse this number. If the application software 26 determines, in step 175, that the user has responded "no", program control is returned to step 166 where the user is prompted to enter a new specimen identification number. If the application software 26 determines, in step 175, that the user has responded "yes", program control continues with step 176 where any previous collection data for the specimen identification number stored in sequential data files 28 is deleted. Program control then continues with step 178.

Figure 13:
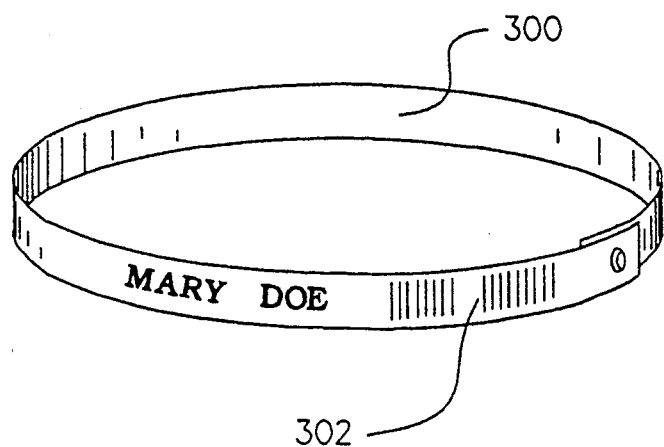
FIG. 13 illustrates a patient identification bracelet with which the present invention is used.

If the application software 26 determines, in step 172, that the specimen identification number needs to be processed, program control continues with step 178 where the patient identification number 52 and patient name 54 associated with the specimen identification number 50 located in the patient collection list 48 are displayed on LCD screen 38. The user is then prompted, in step 180, to enter the patient identification number as verification of the correct patient. This entry may be done manually through keyboard 40 or by using the bar code reader 42 and a bar code 302 (FIG. 13) imprinted on the patient's identification bracelet 300 (FIG. 13). In step 182, the application software 26 determines whether the patient identification number entered in step 180 matches the patient identification number 52 in the patient collection list 48 that is associated with the specimen identification number 50 currently being processed. If the numbers do not match, program control continues with step 184 where a message notifying the user of the mismatch is displayed on LCD screen 38; an audible signal is generated and red LED 46 is illuminated. Program control is then transferred back to step 166 where the user is prompted for a new specimen identification number.

Figure 7:
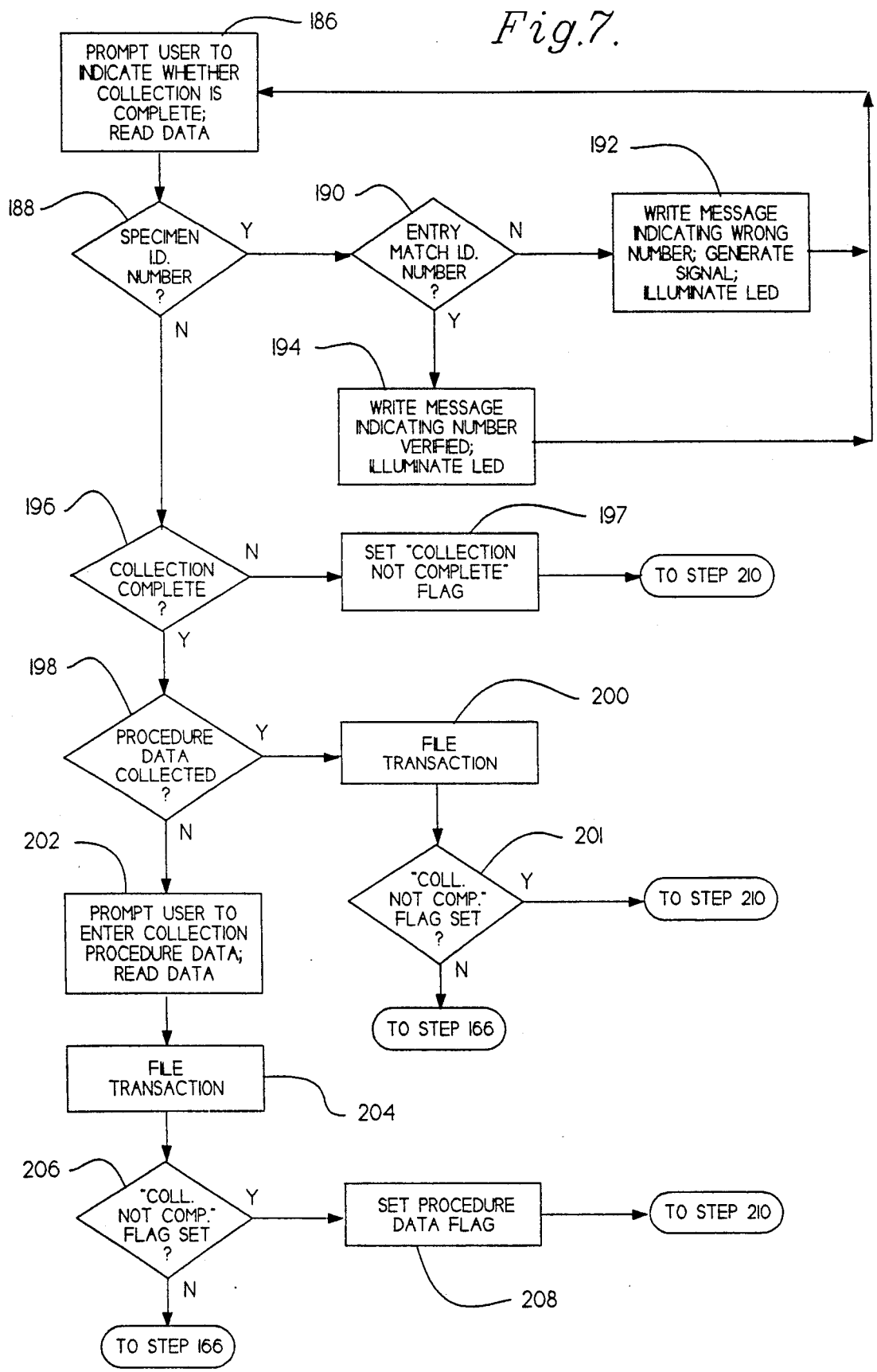

If the patient identification number entered in step 180 matches the patient identification number 52 stored in the patient collection list 48, program control continues with step 186 illustrated in FIG. 7 where the user is prompted to indicate whether the sample collection as specified on the specimen labels 304 (FIG. 14) is complete. The user may either respond "yes", "no" or he may enter the specimen identification number from the specimen label for verification. In step 188, the application software 26 determines whether a specimen identification number was entered by the user. If the user entry was a specimen identification number, then the application software 26 determines, in step 190, whether the specimen identification number entered in step 186 matches the specimen identification number 50 currently being processed. If the numbers do not match, program control continues with step 192 where a message is written to the LCD screen 38 indicating that the wrong specimen identification number has been entered; an audible signal is generated and a red LED 46 is illuminated to warn the user of the error. If the numbers match, a message is written to the LCD screen 38, in step 194, indicating that the specimen identification number has been verified; green LED 44 is illuminated to alert the user that the specimen identification number has been verified.

If the response to the prompt in step 186 was not a specimen identification number, then the application software 26 determines, in step 196, whether the response was "yes" or "no". If the response was "no", a "collection not complete" flag is set in step 197 and program control is then transferred to step 210 shown in FIG. 8. If the response was "yes", program control continues with step 198 where the application software 26 determines whether collection procedure data has previously been entered for the specimen identification number 50 currently being processed. This determination is made by testing a procedure data flag. If the procedure data flag is set, procedure data has been entered; if the procedure data flag is not set, procedure data has not been entered. If collection procedure data has previously been entered, program control continues with step 200 where the transaction is filed. The transaction is filed by storing the specimen identification number 50, collection procedure data and the current date and time in sequential data files 28. Program control then continues with step 201 where the application software 26 determines whether the "collection not complete" flag is set. If the flag is not set, program control is returned to step 166 where the user is prompted for another specimen identification number. If the flag is set, program control is transferred to step 210 shown in FIG. 8. If the collection procedure data has not previously been entered, program control continues with step 202 where the user is prompted to enter collection procedure data. This data consists of an alphanumeric code identifying the type of procedure performed, e.g., "VP" for venipuncture, and a numeric entry indicating the number of times that the procedure was performed. Program control continues with step 204 where the transaction is filed by storing the specimen identification number 50, collection procedure data and the current data and time in sequential data files 28. The application software 26 then determines, in step 206, whether the "collection not complete" flag is set. If the flag is not set, program control is returned to step 166 where the user is prompted for another specimen identification number. If the flag is set, the procedure data flag is set in step 208 and program control is then transferred to step 210 shown in FIG. 8.

Figure 8:
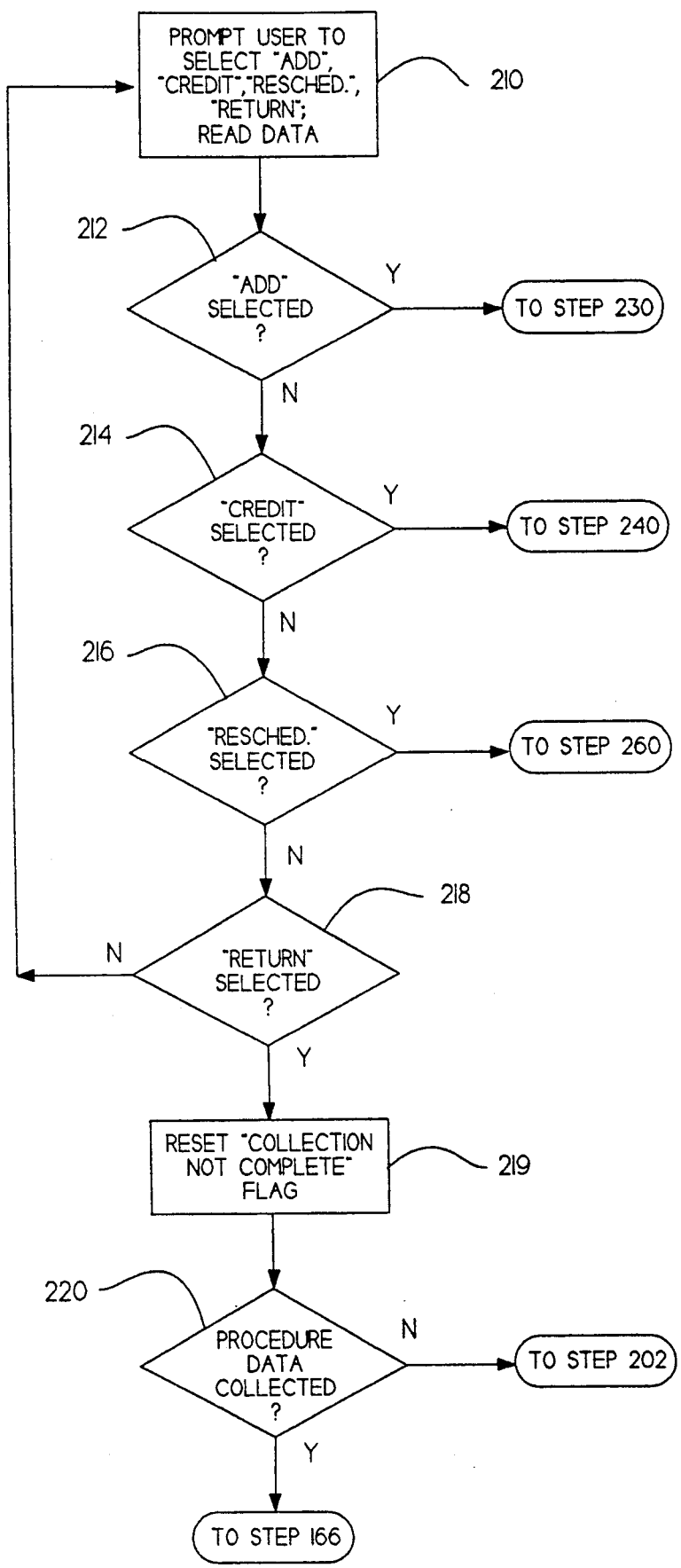

If the application software 26 determines, in step 196, that the sample collection is not complete, program control is transferred to step 210 shown in FIG. 8 where the user is prompted via LCD screen 38, to select one of the following options: "Add", "Credit", "Reschedule" or "Return". The application software 26 determines, in step 212, whether the "Add" function has been selected. If the "Add" function has been selected, program control is transferred to step 230 shown in FIG. 9. If the "Add" function has not been selected, program control continues with step 214 where the application software 26 determines whether the "Credit" function has been selected. If the "Credit" function has been selected, program control is transferred to step 240 shown in FIG. 10. If the "Credit" function has not been selected, program control continues with step 216 where the application software 26 determines whether the "Reschedule" function has been selected. If the "Reschedule" function has been selected, program control is transferred to step 260 shown in FIG. 11. If the "Reschedule" function has not been selected, program control continues with step 218 where the application software 26 determines whether the "Return" function was selected. If the "Return" function has not been selected, program control is returned to step 210 where the user is again prompted to select one of the functions "Add", "Credit", "Reschedule" or "Return". If the "Return" function has been selected, the "collection not complete" flag is reset in step 219. The application software 26 then determines, in step 220, whether the collection procedure data has previously been collected. This determination is made by testing the procedure data flag. If the collection procedure data has not previously been entered, program control returns to step 202 where the user is prompted to enter this information. If the collection procedure data has previously been entered, program control returns to step 166 where the user is prompted to enter a new specimen identification number.

Figure 9:
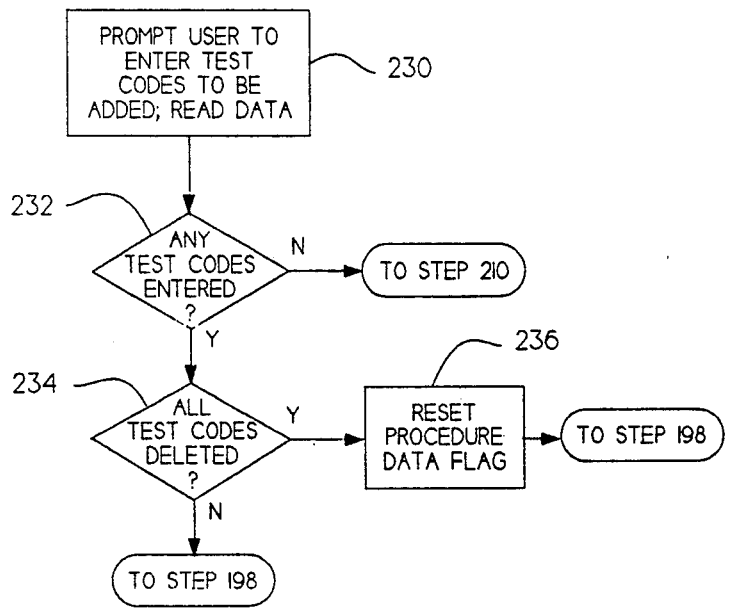
Figure 3:
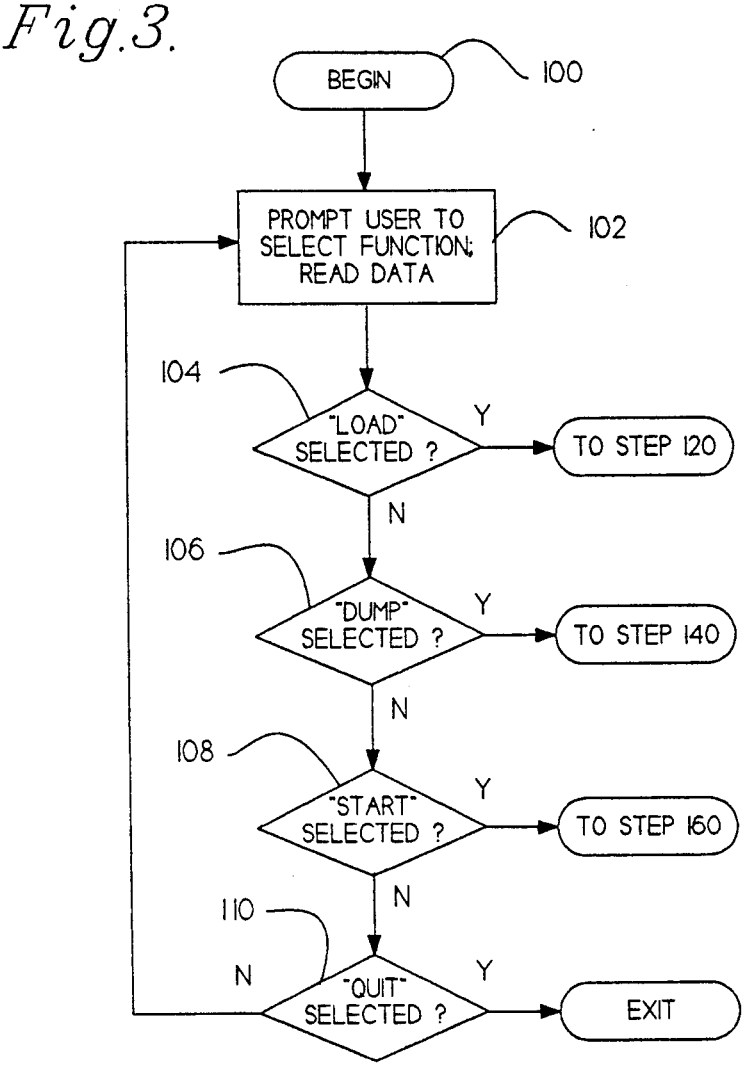

If the application software 26 determines in step 212 that the "Add" function has been selected, program control continues with step 230 shown in FIG. 9 where the user is prompted to enter the alphanumeric test codes, e.g., "NA1" for a sodium test, for additional tests not specified on the specimen label 304 (FIG. 14) that are to be performed on the specimens which have been collected. These codes are entered successively with either a comma or an "enter" key serving as the delimiter. Two successive "enter" characters indicate that the entry process is complete. The application program 26 then determines, at step 232, whether any test codes were entered. If no test codes have been entered, program control returns to step 210 where the user is prompted to select one of the functions "Add", "Credit", "Reschedule" or "Return". If the application software determines, at step 232, that test codes were entered, program control continues with step 234 where the application software 26 determines whether all test codes were previously credited or rescheduled. If not all of the test codes were deleted, program control is returned to step 198. If all of the test codes were deleted, the procedure data flag is reset in step 236 and program control is then returned to step 198. After program control has been returned to step 198, the current transaction will be filed either in step 200 or step 204 depending upon whether collection procedure data has previously been entered. In this case, the alphanumeric test codes for tests that were added in step 230 will be stored in sequential data files 28 along with the specimen identification number 50, collection procedure data and the current date and time.

Figure 10:
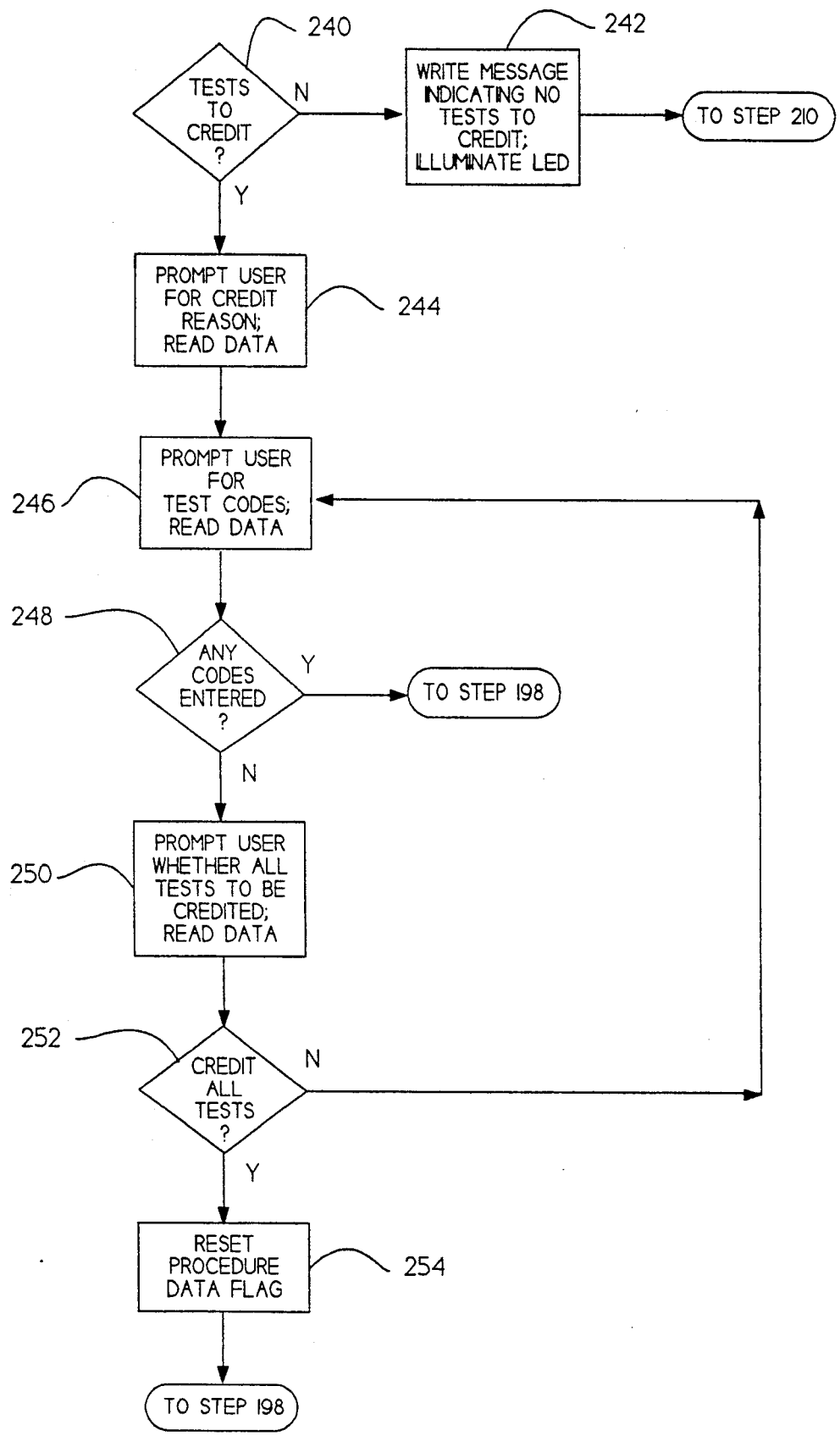

If the application software 26 determines, in step 214, that the "Credit" function was selected, program control continues with step 240 shown in FIG. 10 where the application software 26 determines whether there are any tests which can be credited. If there are no tests which can be credited, program control continues with step 242 where a message is written to the LCD screen 38 indicating that there are no tests which can be credited. A red LED 46 is illuminated to warn the user of this situation. Program control is then returned to step 210 where the user is prompted to select one of the functions "Add", "Credit", "Reschedule" or "Return".

If there are tests which may be credited, the user is prompted for a credit reason in step 244. This data consists of an alphanumeric code identifying the credit reason, e.g., "DI" for patient discharge. The user is then prompted, in step 246, to enter the alphanumeric codes for the tests that are to be credited. These test codes are entered successively with either a comma or an "enter"

key serving as the delimiter. Two successive "enter" characters indicate that the entry process is complete. The application software 26 then determines, in step 248, whether any test codes have been entered. If test codes were entered, program control is transferred to step 198 shown in FIG. 7. If no test codes were entered, program control continues with step 250 where the user is prompted to indicate whether all tests are to be credited. The application software 26 determines, in step 252, whether the user has indicated that all tests are to be credited. If the user responds "no", program control returns to step 246 where the user is again prompted to enter the test codes to be credited. If the user responds "yes", the procedure data flag is reset and program control is returned to step 198. After program control has been returned to step 198, the current transaction will be filed either in step 200 or step 204 depending upon whether collection procedure data has previously been entered. In this case, the alphanumeric test codes for the tests that are to be credited as well as the alphanumeric codes for credit reasons will be stored in sequential data files 28 along with the specimen identification number 50, collection procedure data and the current date and time.

If the application software 26 determines, in step 216, that the reschedule function was selected, program control is transferred to step 260 shown in FIG. 11 where the application software 26 determines whether there are any tests which can be rescheduled. If there are no tests which can be rescheduled, program control continues with step 262 where a message is written to the LCD screen 38 indicating that there are no tests which can be rescheduled. A red LED 46 is illuminated to warn the user of this situation. Program control is then returned to step 210 where the user is prompted to select one of the functions "Add", "Credit", "Reschedule" or "Return".

If there are tests to reschedule, the user is prompted, in step 264, to enter the reschedule time according to a 24 hour clock. In step 266, the application software 26 checks whether the entry for hours is greater than 23 and whether the entry for minutes is greater than 59. If either parameter is out of range, program control continues with step 268 where a message indicating that the entered time is out of range is displayed on LCD screen 38; program control is then returned to step 260. If both parameters are within range, the applications software 26, in step 270, determines whether the entered time is earlier than the present time. If the entered time is earlier than the present time, program control continues with step 272 where a message indicating that the entered time is earlier than the present time is displayed on LCD screen 38, program control is then returned to step 260.

If the entered time is not earlier than the present time, program control continues with step 274 where the user is prompted to enter a reschedule reason. This data consists of an alphanumeric code identifying the reschedule reason, e.g., "NA" for patient not available. Program control continues with step 276 where the user is prompted to enter the alphanumeric codes for the tests that are to be rescheduled. These codes are entered successively with either a comma or an "enter" key serving as the delimiter. Two successive "enter" characters indicate that the entry process is complete. Program control continues with step 278 where the application software 26 determines whether any test codes were entered. If test codes were entered, program control is transferred to step 198. If no codes were entered, program control continues with step 280 where the user is prompted to indicate whether all tests are to be rescheduled. The application software 26 determines, in step 282, whether the user has responded that all tests are to be rescheduled. If the application software 26 determines that the user has indicated that not all tests are to be rescheduled, program control returns to step 276 where the user is again prompted to enter the test codes to be rescheduled. If all tests are to be rescheduled, program control continues with step 284 where the procedure data flag is reset. Program control then transferred to step 198. After program control has been returned to step 198, the current transaction will be filed either in step 200 or step 204 depending upon whether collection procedure data has previously been entered. In this case, the alphanumeric test codes for the tests that are to be rescheduled, the alphanumeric codes for the reschedule reasons and the reschedule times will be stored in the sequential data files 28 along with the specimen identification number 50, collection procedure data and the current date and time.

While the present invention has been described in connection with an exemplary embodiment thereof, it will be understood that many modifications and variations will be readily apparent to those of ordinary skill in the art. This disclosure and the following claims are intended to cover all such modifications and variations.

What I claim as my invention is:

1. A portable data collection system for collecting data relating to medical specimens, comprising:
   input means for receiving first identifying information from a medical specimen label identifying a medical specimen and for receiving second identifying information from a patient's person identifying a patient;
   memory means for storing verification information, said verification information including information relating medical specimens to patients;
   means responsive to said input means and said memory means for comparing said verification information to said first identifying information and for confirming that the medical specimen identified by said first identifying information is to be collected from the patient identified by said second identifying information;
   output means responsive to said means for comparing for indicating whether the medical specimen identified by said first identifying information is to be collected from the patient identified by said second identifying information;
   first means responsive to user data entry at said input means for selectively storing in said memory means information identifying a time at which the confirmed medical specimen is collected from the patient;
   second means responsive to user data entry at said input means for selectively storing in said memory means information identifying alphanumeric codes relating to procedures performed in collecting the confirmed medical specimen from the patient; and
   third means responsive to suer data entry at said input means for selectively storing in said memory means information identifying data relating to laboratory tests to be performed on the confirmed medical specimen.

2. The system of claim 1 additionally comprising fourth means responsive to user data entry at said input means for storing in said memory means information identifying a user performing collection of the medical specimen.

3. The system of claim 1 additionally comprising fifth means responsive to user data entry at said input means for selectively storing in said memory means information identifying data relating to rescheduling collection of the confirmed medical specimen.

4. The system of claim 3 wherein said fifth means includes means responsive to user data entry at said input means for selectively storing in said memory means information identifying the time at which the confirmed medical specimen will be collected.

5. The system of claim 1 wherein said third means includes means responsive to user data entry at said input means for selectively storing in said memory means information identifying data relating to laboratory tests to be added to a laboratory work order and means responsive to user data entry at said input means for selectively storing in said memory means information identifying data relating to laboratory tests to be deleted from the laboratory work order.

6. The system of claim 1 wherein said input means includes means for scanning a bar code and wherein said first identifying information includes a bar code representing a medical specimen identification number on the medical specimen label and said second identifying information includes a bar code representing a patient identification number located on the patient's person.

7. The system of claim 1 wherein said input means includes a keyboard for inputting a medical specimen identification number and a patient identification number.

8. The system of claim 1 wherein said output means includes means for generating an audible signal, an LED and means for displaying a message.

9. A method for collecting data relating to medical specimens, comprising the steps of:
receiving first identifying information from a medical specimen label identifying a medical specimen;
storing verification information, said verification information including information relating medical specimens to patients;
comparing said verification information to said first identifying information to identify a patient associated with the medical specimen;
receiving second identifying information from a patient's person identifying a patient;
confirming that the medical specimen identified by said first identifying information is to be collected from the patient identified by said second identifying information;
indicating whether the medical specimen identified by said first identifying information is to be collected from the patient identified by said second identifying information;
selectively storing in response to user data entry information identifying a time at which the confirmed medical specimen is collected from the patient;
selectively storing in response to user data entry information identifying alphanumeric codes relating to procedures performed in collecting the confirmed medical specimen from the patient; and
selectively storing in response to user data entry information identifying data relating to laboratory tests to be performed on the confirmed medical specimen.

10. The method of claim 9 additionally comprising the step of storing in response to user data entry information identifying a user performing collection of the medical specimen.

11. The method of claim 9 additionally comprising the step of selectively storing in response to user data entry information identifying data relating to rescheduling collection of the confirmed medical specimen.

12. The method of claim 11 wherein said step of selectively storing information identifying data relating to rescheduling collection of the medical specimen includes the step of selectively storing in response to user data entry information identifying the time at which the confirmed medical specimen will be collected.

13. The method of claim 9 wherein said step of selectively storing information identifying data relating to laboratory tests to be performed on the medical specimen includes the step of selectively storing in response to user data entry information identifying data relating to laboratory tests to be added to a laboratory work order and the step of selectively storing in response to user data entry information identifying data relating to laboratory tests to be deleted from the laboratory work order.

14. The method of claim 9 wherein said step of receiving first identifying information includes the step of scanning a bar code and said step of receiving second identifying information includes the step of scanning a bar code and wherein said first identifying information includes a bar code representing a medical specimen identification number on the medical specimen label and said second identifying information includes a bar code representing a patient identification number located on the patient's person.

15. The method of claim 9 wherein said step of indicating includes the step of generating an audible signal, illuminating an LED and displaying a message.

* * * * *

UNITED STATES PATENT AND TRADEMARK OFFICE
CERTIFICATE OF CORRECTION

PATENT NO. : 5,171,977
DATED : December 15, 1992
INVENTOR(S) : Robert L. Morrison It is certified that error appears in the above-identified patent and that said Letters Patent is hereby corrected as shown below:

Col. 2, line 55, after "present", insert "invention".

Col. 4, line 56, delete "men," and substitute therefor --men--.

Col. 10, line 62, delete "suer" and substitute therefor --user--.

Signed and Sealed this

Sixteenth Day of November, 1993

Attest:

BRUCE LEHMAN

Attesting Officer      Commissioner of Patents and Trademarks